United States Patent [19]

Nezót et al.

[11] Patent Number: 4,501,894

[45] Date of Patent: Feb. 26, 1985

[54] HETEROCYCLIC ALCOHOLS AND THEIR DERIVATIVES

[75] Inventors: Francois Nezót, Thiais; Pierre Girault, Paris; Jean Tessier, Vincennes; Jacques Martel, Bondy, all of France

[73] Assignee: Roussel Uclaf, Paris, France

[21] Appl. No.: 352,256

[22] Filed: Feb. 25, 1982

[30] Foreign Application Priority Data

Feb. 26, 1981 [FR] France .................. 81 03830

[51] Int. Cl.$^3$ .......................................... C07D 277/34
[52] U.S. Cl. ........................... 548/186; 548/125; 548/129; 548/136; 548/182; 548/189; 548/202; 548/203; 548/205
[58] Field of Search .......... 548/128, 129, 136, 186, 548/182, 189, 202, 203, 205

[56] References Cited

U.S. PATENT DOCUMENTS

| | | | |
|---|---|---|---|
| 3,538,107 | 11/1970 | Hepworth | 548/202 |
| 3,573,317 | 3/1971 | Smith | 548/128 |
| 3,957,809 | 5/1976 | Hardy et al. | 424/270 |
| 4,051,249 | 9/1977 | Hardy et al. | 424/270 |

FOREIGN PATENT DOCUMENTS

| | | | |
|---|---|---|---|
| 2719561 | 11/1977 | Fed. Rep. of Germany | 548/182 |
| 1452171 | 7/1965 | France | 548/205 |
| 38-25382 | 11/1963 | Japan | 548/129 |

Primary Examiner—Robert Gerstl
Attorney, Agent, or Firm—Charles A. Muserlian

[57] ABSTRACT

Novel heterocyclic compounds of the formula

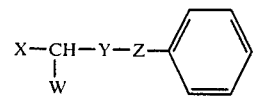

wherein X is selected from the group consisting of chlorine, bromine, iodine and —OH, W is selected from the group consisting of hydrogen and —CN, Z is selected from the group consisting of —CH$_2$— and —O— attached to the carbon atom included between a nitrogen and the sulfur atom of Y and Y is selected from the group consisting of thiazolyl or thiadiazolyl connected to

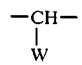

at one of its available positions except for (2-benzyl-4 and 5-thiazolyl) methanol and α-cyano-(2-benzyl-5-thiazolyl)-methanol and the compounds wherein X is halogen when W is —CN whose esters have insecticidal activity.

2 Claims, No Drawings

HETEROCYCLIC ALCOHOLS AND THEIR DERIVATIVES

STATE OF THE ART

U.S. Pat. Nos. 4,051,249 and 3,957,809 describe thiazolic compounds which differ from the compounds of formula I by the substituent in the 2-position which is not an alkyl. French Pat. No. 2,248,835 relates to thiazole substituted carboxylic acids and salts and esters thereof.

OBJECTS OF THE INVENTION

It is an object of the invention to provide the novel heterocyclic compounds of formula I and to provide a novel method for their preparation.

These and other objects and advantages of the invention will become obvious from the following detailed description.

THE INVENTION

The novel heterocyclic compounds of the invention have the formula

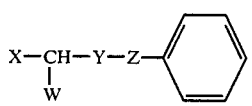

wherein X is selected from the group consisting of chlorine, bromine, iodine and —OH, W is selected from the group consisting of hydrogen and —CN, Z is selected from the group consisting of —CH$_2$— and —O— attached to the carbon atom included between a nitrogen and the sulfur atom of Y and Y is selected from the group consisting of thiazolyl or thiadiazolyl connected to

at one of its available positions except for (2-benzyl-4 and 5-thiazolyl) methanol and α-cyano-(2-benzyl-5-thiazolyl)-methanol and the compounds wherein X is halogen when W is —CN.

Preferred compounds of formula I are those wherein W is hydrogen, Y is

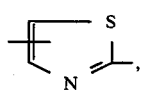

and Z is oxygen, those wherein W is hydrogen, Y is

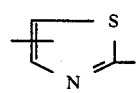

and Z is —CH$_2$— except (2-benzyl-5-thiazolyl)-methanol and those wherein W is —CN, Y is

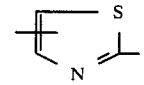

and Z is —O—. Specific preferred compounds of formula I are (2-phenoxy-5-thiazolyl)methanol, 3-chloromethyl-5-phenoxy-(1,2,4)-thiadiazole and (R,S)α-cyano-(2-benzyl-4-thiazolyl)-methanol.

The process of the invention for the preparation of a compound of formula I wherein W is hydrogen, X is —OH, Z is —CH$_2$— and Y is

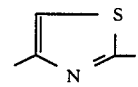

or (2-benzyl-4-thiazolyl)-methanol comprises reacting ethyl bromo pyruvate and phenyl thioacetamide to obtain ethyl 2-benzyl-thiazole-4-carboxylate and reacting the latter a reducing hydride to obtain the corresponding compound of formula I.

The process of the invention for the preparation of a compound of formula I wherein W is hydrogen, X is —OH, Z is —O— and Y is

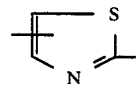

comprises reacting an alkali metal phenate with a compound of the formula

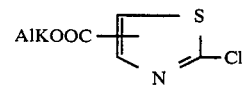

wherein AlK is alkyl of 1 to 6 carbon atoms to obtain a compound of the formula

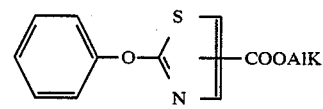

A and reacting the latter with a reducing hydride to obtain the corresponding compound of formula I.

The process of the invention for the preparation of the compound of formula I wherein W is hydrogen, X is —Cl, Z is —O— and Y is

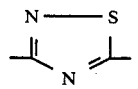

or 3-chloromethyl-5-phenoxy-(1,2,4)-thiadiazole comprises reacting an alkali metal phenate and 3-chloromethyl-5-chloro-(1,2,4)-thiadiazole.

The process for the preparation of a compound of formula I wherein W is hydrogen, Z is —O—, X is —Cl and Y is

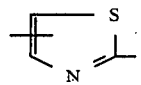

comprises reacting an alkali metal phenate and the corresponding 2-chloro compound.

The process of the invention for the preparation of the compound of formula I wherein W is hydrogen, X is —Cl, Z is —CH$_2$— and Y is

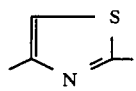

comprises reacting dichloroacetone and phenyl thioacetamide to obtain a compound of the formula

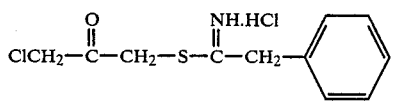

and cyclizing the latter with concentrated sulfuric acid.

The process of the invention for the preparation of the compound of formula I wherein W is hydrogen, X is —Cl, Z is —CH$_2$— and Y is

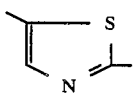

comprising reacting (2-benzyl-5-thiazolyl)-methanol with phosphorus pentachloride or phosphorus oxychloride.

The process of the invention to obtain the compound of formula I wherein W is hydrogen, X is —Cl, Z is —CH$_2$— and Y is

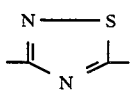

comprises reacting chloroacetamidine hydrochloride and ethyl phenylthioacetate in the presence of sodium ethylate.

The process of the invention for the preparation of the compound of formula I wherein W is hydrogen, X is —OH, Z is —O— or —CH$_2$— and Y is

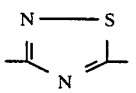

comprises subjecting the corresponding 3-chloromethyl compound to acid or basic hydrolysis.

The process of the invention for the preparation of a compound of formula I wherein X is iodine or bromine comprises treating the corresponding chloro compound with potassium iodide or potassium bromide.

The process of the invention for the preparation of a compound of the formula

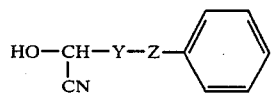

wherein Y and Z have the above definition comprises reacting a compound of the formula

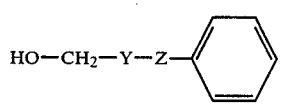

with manganese dioxide to obtain a compound of the formula

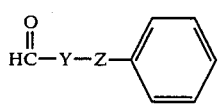

and reacting the latter in an aqueous acid medium with a compound capable of generating CN$^-$ ions.

In a preferred embodiment of the processes of the invention, the reducing hydride is diethyl sodium aluminum dihydride and the alkali metal phenate is sodium phenate or potassium phenate. The AlK in the compounds of formula A is preferably ethyl and the generation of the CN$^-$ is effected with an alkali metal cyanide in the presence of an acid. The hydrolysis of the 3-chloro-methyl compounds is effected with a base such as sodium carbonate or potassium carbonate or sodium hydroxide or potassium hydroxide or an acid such as hydrochloric acid.

The compounds of formula I are useful for the preparation of esters of the formula

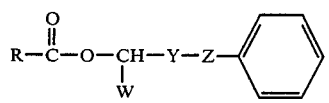

wherein W, Y and Z have the above definitions and R is an acyl of an organic carboxylic acid such as

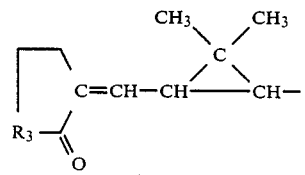

wherein R$_3$ is selected from the group consisting of —O—, —S— and —NH— which esters have insecticidal activity as described in copending, commonly assigned U.S. patent application Ser. No. 352,257 filed on even date herewith now U.S. Pat. No. 4,450,164.

The esters may be prepared by reacting a compound of formula I or a functional derivative thereof with an acid of the RCOOH wherein R has the above definition or a functional derivative thereof by known esterification techniques.

The compounds of formula II have been shown to have insecticidal activity against flies, spodoptera and epilachna and acaricidal activity against Tetranychus urticae.

In the following examples there are described several preferred embodiments to illustrate the invention. However, it is to be understood that the invention is not intended to be limited to the specific embodiments.

EXAMPLE 1

(2-benzyl-4-thiazolyl)-methanol

STEP A: Ethyl 2-benzyl-thiazole-4-carboxylate 40 g of ethyl bromopyruvate were progressively added to a mixture of 30.2 g of phenylthioacetamide, 120 ml of ethanol and 20 ml of pyridine and the mixture was refluxed for 16 hours. The mixture was evaporated to dryness under reduced pressure and the residue was added to a water-ether mixture. The mixture was stirred and the decanted aqueous phase was extracted with ether. The combined organic phases were evaporated to dryness and the residue was chromatographed over silica gel. Elution with a 7-3 hexane-ethyl acetate mixture yielded 22.5 g of ethyl 2-benzyl-thiazole-4-carboxylate melting at 78°–79° C.

STEP B: (2-benzyl-4-thiazolyl)-methanol 90 ml of a toluene solution of 2M/liter of diethyl sodium aluminum dihydride were added dropwise at −10° C. to a solution of 20 g of the product of Step A in 100 ml of toluene and the mixture was stirred at −5° C. for one hour. 150 ml of aqueous 2N hydrochloric acid were added dropwise to the mixture at −20° C. and then ether and water were added thereto. The mixture was filtered and the organic phase of the filtrate was washed with water, dried and evaporated to dryness. The residue was chromatographed over silica gel and was eluted with a 7-3 methylene chloride-ethyl acetate mixture to obtain 13.6 g of (2-benzyl-4-thiazolyl)-methanol melting about 50° C.

IR Spectrum (chloroform): Absorption at 3595 cm$^{-1}$ (OH); at 1690, 1616 and 1586 cm$^{-1}$ (C=C, C=N and aromatic); at 1568, 1536 and 1487 cm$^{-1}$ (aromatic ring).

EXAMPLE 2

(2-phenoxy-4-thiazolyl)-methanol

Step A: Ethyl 2-phenoxy-thiazole-4-carboxylate

A mixture of 2 g of ethyl 2-chloro-thiazole-4-carboxylate, 2.5 ml of hexamethyl phosphorotriamide, 50 ml of dimethylformamide and 1.5 g of sodium iodide was heated at 100° C. for one hour and was cooled to 20° C. 1.32 g of potassium phenate were added in portions to the mixture which was then refluxed for 90 minutes and then was cooled. Water and ethyl acetate were added to the mixture and the decanted aqueous phase was extracted with ethyl acetate. The organic phase was washed with water and evaporated to dryness. The residue was chromatographed over silica gel and was eluted with a 7-3-1 hexane-isopropyl ether-triethylamine mixture to obtain 1.08 g of ethyl 2-phenoxy-thiazole-carboxylate melting at 67° C.

STEP B: (2-phenoxy-4-thiazolyl)-methanol 54 ml of a toluene solution of 2M/liter of diethyl sodium aluminum dihydride were slowly added at −10° C. to a solution of 12 g of ethyl 2-phenoxy-thiazole-carboxylate in 60 ml of toluene and the mixture was stirred at −5° C. for one hour. 80 ml of aqueous 2N hydrochloric acid were added at −20° C. to the mixture followed by addition of water and filtration. The decanted organic phase was washed with water and evaporated to dryness. The residue was chromatographed over silica gel and eluted with an 8-2 methylene chlorideethyl acetate mixture to obtain 8.15 g of (2-phenoxy-4-thiazolyl)-methanol.

IR Spectrum (chloroform): Absorption at 3590 cm$^{-1}$ (OH); at 1551, 1530, 1503 and 1486 cm$^{-1}$ (aromatic ring and thiazolyl); at 690 cm$^{-1}$ (phenyl-deformation).

NMR Spectrum (deuterochloroform): Peaks at 4.5 ppm (hydrogens of CH$_2$O); at 3.5 ppm (hydrogen of —OH); at 6.66 ppm (hydrogen of thiazolic); at 7.10 to 7.50 ppm (hydrogens of aromatic ring).

EXAMPLE 3

(2-phenoxy-5-thiazolyl)-methanol

STEP A: Ethyl 2-phenoxy-thiazole-5-carboxylate

A mixture of 3.8 g of ethyl 2-chloro-thiazole-5-carboxylate, 3 g of sodium iodide and 50 ml of acetonitrile was refluxed for one hour and 2.6 g of potassium phenate were added thereto. The mixture was refluxed for 24 hours and concentrated. Water was added to the mixture which was then extracted with ethyl acetate. The organic phase was dried and evaporated to dryness. The residue was chromatographed over silica gel and eluted with a 9-1 benzene-ethyl acetate mixture to obtain 3 g of ethyl 2-phenoxy-thiazole-5-carboxylate.

IR Spectrum (chloroform): Absorption at 1710 cm$^{-1}$ (C=O); at 1537 cm$^{-1}$ (C=C and C=N); at 1595-1491 cm$^{-1}$ (aromatic ring).

STEP B: (2-phenoxy-5-thiazolyl)-methanol

A solution of 12 g of the product of Step A in 100 ml of tetrahydrofuran was added dropwise to a mixture of 2.8 g of lithium aluminum hydride in 200 ml of tetrahydrofuran and the mixture was refluxed for 24 hours. Excess hydride was destroyed by addition of ethyl acetate and aqueous 2N hydrochloric acid was added thereto. The mixture was filtered and the aqueous phase was extracted with ether. The combined organic phases were evaporated to dryness to obtain 5.2 g of (2-phenoxy-5-thiazolyl)-methanol.

IR Spectrum (chloroform): Absorption at 3590 cm$^{-1}$ (OH); at 1606, 1599, 1500 and 1481 cm$^{-1}$ (aromatic ring and conjugated system).

NMR Spectrum (deuterochloroform): Peaks at 4.64–4.65 ppm (hydrogens of methylene of alcohol); at 4.75 ppm (hydrogen of —OH); at 6.7 to 7.5 ppm (hydrogens of phenyl).

EXAMPLE 4

3-chloromethyl-5-phenoxy-[1,2,4]-thiadiazole 5.8 g of sodium phenate were added to a mixture of 50 ml of benzene, 10 ml of dimethylformamide and 8.5 g of 3-chloromethyl-5-chloro-[1,2,4]-thiadiazole and the mixture was stirred at 20° C. for 24 hours. 50 ml of water were added to the mixture and the decanted aqueous phase was extracted with benzene. The combined organic phase was dried and evaporated to dryness. The oil residue was distilled under reduced pressure to obtain 7.2 g of 3-chloromethyl-5-phenoxy-[1,2,4]-thiadiazole boiling at 114°–116° C. at 0.5 mm Hg.

EXAMPLE 5

(R,S)α-cyano-(2-benzyl-4-thiazolyl)-methanol

STEP A: (2-benzyl-4-thiazolyl)-methanal 2.1 g of manganese dioxide were added to a mixture of 0.5 g of (2-benzyl-4-thiazolyl)-methanol and 10 ml of benzene and the mixture was stirred at 20° C. for 20 hours and was filtered. The filtrate was evaporated to dryness and the residue was chromatographed over silica gel. Elution with a 7-3 hexane-ethyl acetate mixture yielded 0.3 g of (2-benzyl-4-thiazolyl)-methanal melting at 78° C.

STEP B: (R,S) α-cyano-(2-benzyl-4-thiazolyl)-methanol

A solution of 2.8 g of the product of Step A in 10 ml of ether was added at 10° C. to a solution of 0.98 g of sodium cyanide in 5 ml of water and the mixture was stirred at 10° C. for 10 minutes. Then, a solution of 2 ml of concentrated sulfuric acid in 3 ml of water was added dropwise to the mixture at 0° C. and the mixture was stirred at 0° C. for 2 hours. Water and ethyl acetate were added to the mixture and the decanted organic phase was washed with water, dried and evaporated to dryness under reduced pressure. The residue was added to hexane and the mixture was stirred for one hour and was vacuum filtered. The precipitate was dried to obtain 2.76 g of (R,S) α-cyano-(2-benzyl-4-thiazolyl)-methanol melting at 98° C.

EXAMPLE 6

(R,S)α-cyano-(2-phenoxy-5-thiazolyl)-methanol

STEP A: (2-phenoxy-5-thiazolyl)-methanol 40 g of managese dioxide were added to a solution of 10 g of (2-phenoxy-5-thiazolyl)-methanol in 250 ml of benzene and the mixture was stirred at 40° C. for 5 hours and was filtered. The filtrate was evaporated to dryness and the residue was chromatographed over silica gel. Elution with a 7-3 methylene chloride-ethyl acetate mixture yielded 7.7 g of (2-phenoxy-5-thiazolyl)-methanol melting at 50° C.

STEP B: (R,S) α-cyano-(2-phenoxy-5-thiazolyl)-methanol

A solution of 1.7 g of the product of Step A in 6 ml of ether was added at 15° C. to a solution of 0.6 g of sodium cyanide in 10 ml of water and then a solution of 1 ml of aqueous concentrated sulfuric acid in 0.8 ml of water was added dropwise at 5° C. to the mixture. The mixture was stirred at 10° C. for 2 hours and the decanted organic phase was washed with water, dried and evaporated to dryness. The residue was chromatographed over silica gel and eluted with an 8-2 methylene chloride-ethyl acetate mixture to obtain 1.15 g of (R,S) α-cyano-(2-phenoxy-5-thiazolyl)-methanol.

IR Spectrum (chloroform): Absorption at 1665 cm$^{-1}$ (C=O); at 3580 cm$^{-1}$ (OH); at 3560 cm$^{-1}$ (associated OH); at 1590, 1545, 1490 and 1480 cm$^{-1}$ (C=C, C=N and aromatic ring); at 688 cm$^{-1}$ (phenyl).

NMR Spectrum (deuterochloroform): Peaks at 5.57 ppm (hydrogen of —CH—O—); at 5.33 ppm (hydrogen of —OH); at 7.0 to 7.5 ppm (hydrogens of aromatic ring).

EXAMPLE 7

(R,S) α-cyano-(2-phenoxy-4-thiazolyl)-methanol

STEP A: (2-phenoxy-4-thiazolyl)-methanal 19.1 g of manganese dioxide were added to a solution of 4.6 g of (2-phenoxy-4-thiazolyl)-methanol in 100 ml of benzene and the mixture was stirred at 60° C. for 3 hours and was filtered. The filtrate was evaporated to dryness under reduced pressure and the residue was chromatographed over silica gel. Elution with an 8-2 methylene chloride-ethyl acetate mixture yielded 2.6 g of (2-phenoxy-4-thiazolyl)-methanal melting at 63° C.

STEP B: (R,S) α-cyano-(2-phenoxy-4-thiazolyl)-methanol

A solution of 2.4 g of the product of Step A in 10 ml of ether was added at 10° C. to a solution of 0.85 g of sodium cyanide in 5 ml of water and the mixture was stirred for 10 minutes. A solution of 2 ml of aqueous concentrated sulfuric acid in 3 ml of water was added dropwise at 0° C. to the mixture which was then stirred for 2 hours at 0° C. The decanted organic phase was washed with water, dried and evaporated to dryness under reduced pressure. The residue was added to isopropyl ether and the mixture was vacuum filtered. The product was dried to obtain 2.28 g of (R,S)α-cyano-(2-phenoxy-4-thiazolyl)-methanol.

IR Spectrum (chloroform): Absorption at 3580 cm$^{-1}$ (OH); at 3550 cm$^{-1}$ (associated OH); at 1590, 1504 and 1487 cm$^{-1}$ (aromatic ring and thiazole).

NMR Spectrum (deuterochloroform): Peaks at 4.08 ppm (hydrogen of OH); at 5.41 ppm (hydrogen of CH—O—); at 7.33 ppm (phenyl hydrogens); at 7.0 ppm (hydrogen of thiazolyl).

EXAMPLE 18

(2-phenoxy-4-thiazolyl)-methyl (1R,3S) 2,2-dimethyl-3-[(dihydro-2-oxo-3-(2H)-thienylidene)-methyl]-cyclopropane-1-carboxylate 0.11 g of 4-dimethylamino-pyridine and 2 g of dicyclohexylcarbodiimide were added to a solution of 2.04 g of (1R,3S) 2,2-dimethyl-3-[(dihydro-2-oxo-3-(2H)-thienylidene)-methyl]-cyclopropane-1-carboxylic acid [described in French Pat. No. 70-21682] in 20 ml of methylene chloride and the mixture was stirred at 20° C. for 15 minutes. A solution of 1.7 g of (2-phenoxy-4-thiazolyl)-methanol in 10 ml of methylene chloride was added dropwise to the mixture which was stirred at 20° C. for 17 hours and was filtered. The organic phase of the filtrate was washed with water, dried and evaporated to dryness under reduced pressure. The residue was chromatographed over silica gel, and was eluted with an 8-2 cyclohexaneethyl acetate mixture to obtain 2.44 g of (2-phenoxy-4-thiazolyl)-methyl (1R,3S) 2,2-dimethyl-3-[(dihydro-2-oxo-3-(2H)-thienylidene)-methyl]-cyclopropane-1-carboxylate melting at 78° C.

EXAMPLE 9

(2-phenoxy-5-thiazolyl)-methyl (1R,3S) 2,2-dimethyl-3-[(dihydro-2-oxo-3-(2H)-thienylidene)-methyl]-cyclopropane-1-carboxylate 2.1 g of (2-phenoxy-5-thiazolyl)-methanol were added to a solution of 2.44 g of (1R,3S) 2,2-dimethyl-3-](dihydro-2-oxo-3-(2H)-thienylidene)-methyl]-cyclopropane-1-carboxylic acid chloride [described in French Pat. No. 70-21682] in 50 ml of benzene and 3 ml of pyridine were added thereto dropwise at 0° C. The mixture was stirred at 20° C. for 24 hours and was then poured into aqueous 2N hydrochloric acid solution. The decanted organic phase was dried and evaporated to dryness under reduced pressure. The residue was chromatographed over silica gel and was eluted with benzene. The product was crystallized from ethyl acetate to obtain 1.8 g of (2-phenoxy-5-thiazolyl)-methyl (1R,3S) 2,2-dimethyl-3-[(dihydro-2-oxo-3-(2H)-thienylidene)-methyl]-cyclopropane-1-carboxylate.

EXAMPLE 10

(R,S)α-cyano-(2-benzyl-5-thiazolyl)-methyl (1R,3S)2,2-dimethyl-3-[(dihydro-2-oxo-3-(2H)-thienylidene)-methyl]-cyclopropane-1-carboxylate A solution of 0.1 g of 4-dimethylamino-pyridine, 0.89 g of dicyclohexylcarbodiimide, 1 g of (1R,3S) 2,2-dimethyl-3-[(dihydro-2-oxo-3-(2H)-thienylidene)-methyl]-cyclopropane-1-carboxylic acid and 20 ml of ethyl acetate was admixed at 10° C. with a solution of 0.9 g of (R,S)α-cyano-(2-benzyl-5-thiazolyl)-methanol in 25 ml of ethyl acetate and the mixture was stirred at 20° C. for 2 hours and was filtered. The filtrate was washed with aqueous saturated sodium chloride solution and evaporated to dryness under reduced pressure. The residue was chromatographed over silica gel and eluted with a 6-4 cyclohexane-ethyl acetate mixture to obtain 1.18 g of (R,S) α-cyano-(2-benzyl-5-thiazolyl)-methyl (1R,3S)2,2-dimethyl-3-[(dihydro-2-oxo-3-(2H)-thienylidene)-methyl]-cyclopropane-1-carboxylate melting at less than 50° C. The structure was confirmed by IR Spectrum and NMR Spectrum.

INSECTICIDAL ACTIVITY

A. Against *Spodoptera litoralis*

The insecticidal activity of the compound of Example 8 was determined by topical application of an acetone solution of the said compound with an Arnold micromanipulator to the dorsal thorax of larvae of *Spodoptera litoralis* using 15 larvae for each dose. The larvae were in the 4th stage of development and were about 10 days old at 24° C. and 65% relative humidity. After treatment, the larvae were placed in an artifical nutritive medium (Poitout medium) and the number of dead larvae was determined 48 hours later. The $DL_{50}$ in nanograms per insect for the compound of Example 8 was 6.0.

B. Knockdown of house flies

The knockdown activity of the compounds of Examples 9 and 10 against houseflies was determined on female houseflies 4 to 5 days old by direct spraying in one second of 50 insects per dose with 2 ml of a solution of the test product in a mixture of 5% acetone and Isopar L (petrolium solvent) in a Kearn and March cylinder. The readings were taken every minute for 10 minutes and then at 15 minutes and the $KT_{50}$ was determined by known methods. The $KT_{50}$ in minutes was 3.5 and 6.0 for the products of Examples 9 and 10, respectively.

Various modifications of the products and processes of the invention may be made without departing from the spirit or scope thereof and it should be understood that the invention is intended to be limited only as defined in the appended claims.

What we claim is:

1. A compound of the formula

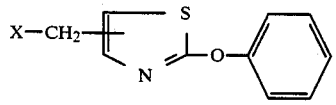

wherein X is selected from the group consisting of chlorine, bromine, iodine and —OH.

2. A compound of the formula

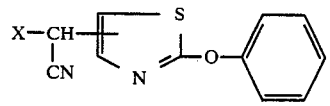

wherein X is selected from the group consisting of chlorine, bromine, iodine and —OH.

* * * * *